United States Patent
Liao

(10) Patent No.: US 7,109,015 B2
(45) Date of Patent: Sep. 19, 2006

(54) REMOVAL OF N-TERMINAL METHIONINE FROM PROTEINS BY ENGINEERED METHIONINE AMINOPEPTIDASE

(75) Inventor: You-Di Liao, Taipei (TW)

(73) Assignee: Academia Sinica, Taipei (TW)

(*) Notice: Subject to any disclaimer, the term of this patent is extended or adjusted under 35 U.S.C. 154(b) by 107 days.

(21) Appl. No.: 10/813,549

(22) Filed: Mar. 29, 2004

(65) Prior Publication Data

US 2005/0214899 A1 Sep. 29, 2005

(51) Int. Cl.
*C12N 9/52* (2006.01)
*C12N 15/57* (2006.01)
*C12N 15/70* (2006.01)
*C12P 21/06* (2006.01)

(52) U.S. Cl. .............. 435/220; 435/68.1; 435/252.3; 435/252.33; 435/320.1; 536/23.2

(58) Field of Classification Search ...... None
See application file for complete search history.

(56) References Cited

U.S. PATENT DOCUMENTS

| | | | | |
|---|---|---|---|---|
| 4,870,017 A | * | 9/1989 | Ben-Bassat et al. | 435/212 |
| 5,013,662 A | | 5/1991 | Ben-Bassat et al. | 435/212 |
| 5,753,465 A | * | 5/1998 | Ho et al. | 435/69.6 |
| 5,885,820 A | * | 3/1999 | Chang | 435/212 |
| 5,888,796 A | * | 3/1999 | Chang | 435/212 |
| 6,071,718 A | * | 6/2000 | Mukerji et al. | 435/69.1 |
| 6,261,794 B1 | * | 7/2001 | Chang | 435/23 |
| 6,362,324 B1 | * | 3/2002 | Kapeller-Libermann et al. | 536/23.2 |
| 6,399,349 B1 | * | 6/2002 | Ryan et al. | 435/226 |
| 6,593,454 B1 | * | 7/2003 | Chang | 530/331 |
| 6,638,750 B1 | * | 10/2003 | Aurora et al. | 435/212 |
| 6,743,600 B1 | * | 6/2004 | Tou et al. | 435/24 |
| 6,794,159 B1 | * | 9/2004 | Tou et al. | 435/68.1 |

FOREIGN PATENT DOCUMENTS

WO   WO 2005/059127 A1 *  6/2005

OTHER PUBLICATIONS

Abe, A., et al. (2000) Acetylation at the N-terminus of actin strengthens weak interaction between actin and myosin. Biochem. Res. Commun., 268:14-19.

Adachi, K., et al. (2000) Expression of functional soluble human α-globin chains of hemoglobin in bacteria. Protein Expr. Purif., 20:37-44.

Belagaje, R.M., et al. (1997) Increased production of low molecular weight recombinant proteins in *Escherichia coli*. Protein Sci., 6:1953-1962.

Ben-Bassat, A., et al. (1987) Processing of the initiation methionine from proteins: properties of the *Escherichia coli* methionine aminopeptidase and its gene structure. J. Bacteriol., 169(2):751-757.

(Continued)

*Primary Examiner*—Nashaat T. Nashed
*Assistant Examiner*—William W. Moore
(74) *Attorney, Agent, or Firm*—Fish & Richardson P.C.

(57) ABSTRACT

The present invention provides methionine aminopeptidases (MetAPs) with a broad substrate range, particularly those capable of removing the N-terminal Met from bulky or acidic penultimate residues. In preferred embodiments, these MetAPs have mutations at the 233, 206 and/or 168 positions of SEQ ID NO:1. Preferably, amino acids at these residues are substituted with glycine or threonine. Also provided are cells comprising the MetAPs, DNA encoding the MetAPs, and methods of using the MetAPs.

27 Claims, 1 Drawing Sheet

OTHER PUBLICATIONS

Boix, E., et al. (1996) Role of the N terminus in RNase A homologues: differences in catalytic activity, ribonuclease inhibitor interaction and cytotoxicity. J. Mol. Biol., 257:992-1007.

Busby, W.H., Jr., et al. (1987) An enzyme(s) that converts glutaminyl-peptides into pyroglutamyl-peptides. Presence in pituitary, brain, adrenal medulla, and lymphocytes. J. Biol. Chem., 262(18):8532-8536.

Chang, S.Y., et al. (1989) Methionine aminopeptidase gene of *Escherichia coli* is essential for cell growth. J. Bacteriol., 171(7):4071-4072.

Chen, S., et al. (2002) The specificity *in vivo* of two distinct methionine aminopeptidases in *Saccharomyces cerevisiae*. Arch. Biochem. Biophys., 398(1):87-93.

Chiu, C.H., et al. (1999) Amino acid residues involved in the functional integrity of *Escherichia coli* methionine aminopeptidase. J Bacteriol 181(15):4686-4689.

Endo, S., et al. (2001) The additional methionine residue at the N-terminus of bacterially expressed human interleukin-2 affects the interaction between the N- and C-termini. Biochemistry, 40:914-919.

Fischer, W.H., and Spiess, (1987) Identification of a mammalian glutaminyl cyclase converting glutaminyl into pyroglutamyl peptides. Proc. Natl. Acad. Sci. U.S.A., 84:3628-3632.

Hirel, P.H., et al. (1989) Extent of N-terminal methionine excision from *Escherichia coli* proteins is governed by the side-chain length of the penultimate amino acid. Proc. Natl. Acad. Sci. U.S.A., 86:8247-8251.

Huang, H.C., et al. (1998) The Rana catesbeiana rcr gene encoding a cytotoxic ribonuclease. Tissue distribution, cloning, purification, cytotoxicity, and active residues for RNase activity. J. Biol. Chem., 273(11):6395-6401.

Hwang, D.D.W., et al. (1999) Co-expression of glutathione S-transferase with methionine aminopeptides: a system of producing enriched N-terminal processed proteins in *Escherichia coli*. Biochem. J., 338(Pt 2):335-342.

Ishitani, M., et al. (2000) SOS3 function in plant salt tolerance requires N-myristoylation and calcium binding. Plant Cell, 12:1667-1677.

Leu, Y.J., et al. (2003) Residues involved in the catalysis, base specificity, and cytotoxicity of ribonuclease from *Rana catesbeiana* based upon mutagenesis and X-ray crystallography. J. Biol. Chem., 278(9):7300-7309.

Li, X., and Chang, Y.H. (1995) Amino-terminal protein processing in *Saccharomyces cerevisiae* is an essential function that requires two distinct methionine aminopeptidases. Proc. Natl. Acad. Sci. U.S.A., 92:12357-12361.

Liao, Y.D., and Wang, J.J. (1994). Yolk granules are the major compartment for bullfrog (*Rana catesbeiana*) oocyte-specific ribonuclease. Eur J Biochem., 222:215-220.

Liao, Y.D., et al. (2000) Purification and cloning of cytotoxic ribonucleases from *Rana catesbeiana* (bullfrog). Nucleic Acids Res., 28(21):4097-4104.

Liao, Y.D., et al. (2003) The structural integrity exerted by N-terminal pyroglutamate is crucial for the cytotoxicity of frog ribonuclease from *Rana pipiens*. Nucleic Acids Res., 31(18):5247-5255.

Lowther, W.T., et al. (1999) *Escherichia coli* methionine aminopeptidase: implications of crystallographic analyses of the native, mutant, and inhibited enzymes for the mechanism of catalysis. Biochemistry, 38:7678-7688.

Lowther, W.T., and Matthews, B.W. (2000) Structure and function of the methionine aminopeptidases. Biochim. Biophys. Acta., 1477:157-167.

Moerschell, R.P., et al. (1990) The specificities of yeast methionine aminopeptidase and acetylation of amino-terminal methionine *in vivo*. Processing of altered iso-1-cytochromes ccreated by oligonucleotide transformation. J. Biol. Chem., 265(32):19638-19643.

Notomista, E., et al. (1999) Effective expression and purification of recombinant onconase, an antitumor protein. FEBS Lett., 463:211-215.

Prchal, J.T., et al. (1986) Hemoglobin Long Island is caused by a single mutation (adenine to cytosine) resulting in a failure to cleave amino-terminal methionine. Proc. Natl. Acad. Sci. U.S.A., 83:24-27.

Roderick, S.L., and Matthews, B.W. (1993) Structure of the cobalt-dependent methionine aminopeptidase from *Escherichia coli*: a new type of proteolytic enzyme. Biochemistry, 32:3907-3912.

Shapiro, R., et al. (1988) Expression of Met-(-1) angiogenin in *Escherichia coli*: conversion to the authentic <Glu-1 protein. Anal. Biochem., 175:450-461.

Tahirov, T.H., et al. (1998) Crystal structure of methionine aminopeptidase from hyperthermophile, *Pyrococcus furiosus*. J. Mol. Biol., 284:101-124.

Tobias, J.W., et al. (1991) The N-end rule in bacteria. Science, 254:1374-1377.

Varshavsky, A. (1996) The N-end rule: functions, mysteries, uses. Proc. Natl. Acad. Sci. U.S.A., 93:12142-12149.

Vetro, J.A., and Chang, Y.H. (2002) Yeast methionine aminopeptidase type 1 is ribosome-associated and requires its N-terminal zinc finger domain for normal function *in vivo*. J. Cell. Biochem., 85:678-688.

Walker, K.W., and Bradshaw, R.A. (1999) Yeast methionine aminopeptidase I. Alteration of substrate specificity by site-directed mutagenesis. J. Biol. Chem., 274(19):13403-13409.

* cited by examiner

SEQUENCE LISTING

<160> NUMBER OF SEQ ID NOS: 21

<210> SEQ ID NO 1
<211> LENGTH: 264
<212> TYPE: PRT
<213> ORGANISM: Escherichia coli

<400> SEQUENCE: 1

Met Ala Ile Ser Ile Lys Thr Pro Glu Asp Ile Glu Lys Met Arg Val
 1               5                  10                  15

Ala Gly Arg Leu Ala Ala Glu Val Leu Glu Met Ile Glu Pro Tyr Val
            20                  25                  30

Lys Pro Gly Val Ser Thr Gly Glu Leu Asp Arg Ile Cys Asn Asp Tyr
        35                  40                  45

Ile Val Asn Glu Gln His Ala Val Ser Ala Cys Leu Gly Tyr His Gly
 50                  55                  60

Tyr Pro Lys Ser Val Cys Ile Ser Ile Asn Glu Val Val Cys His Gly
65                  70                  75                  80

Ile Pro Asp Asp Ala Lys Leu Leu Lys Asp Gly Asp Ile Val Asn Ile
                85                  90                  95

Asp Val Thr Val Ile Lys Asp Gly Phe His Gly Asp Thr Ser Lys Met
            100                 105                 110

Phe Ile Val Gly Lys Pro Thr Ile Met Gly Glu Arg Leu Cys Arg Ile
        115                 120                 125

Thr Gln Glu Ser Leu Tyr Leu Ala Leu Arg Met Val Lys Pro Gly Ile
130                 135                 140

Asn Leu Arg Glu Ile Gly Ala Ala Ile Gln Lys Phe Val Glu Ala Glu
145                 150                 155                 160

Gly Phe Ser Val Val Arg Glu Tyr Cys Gly His Gly Ile Gly Arg Gly
                165                 170                 175

Phe His Glu Glu Pro Gln Val Leu His Tyr Asp Ser Arg Glu Thr Asn
            180                 185                 190

Val Val Leu Lys Pro Gly Met Thr Phe Thr Ile Glu Pro Met Val Asn
        195                 200                 205

Ala Gly Lys Lys Glu Ile Arg Thr Met Lys Asp Gly Trp Thr Val Lys
    210                 215                 220

Thr Lys Asp Arg Ser Leu Ser Ala Gln Tyr Glu His Thr Ile Val Val
225                 230                 235                 240

Thr Asp Asn Gly Cys Glu Ile Leu Thr Leu Arg Lys Asp Asp Thr Ile
                245                 250                 255

Pro Ala Ile Ile Ser His Asp Glu
            260

<210> SEQ ID NO 2
<211> LENGTH: 30
<212> TYPE: DNA
<213> ORGANISM: Artificial Sequence
<220> FEATURE:
<223> OTHER INFORMATION: primer

<400> SEQUENCE: 2
cgcggagctc gatcccgcga aattaatacg                              30

<210> SEQ ID NO 3
<211> LENGTH: 57
<212> TYPE: DNA

```
<213> ORGANISM: Artificial Sequence
<220> FEATURE:
<223> OTHER INFORMATION: primer

<400> SEQUENCE: 3
cttgattgag atagccatta tctccttctt aaagttaaac aaaattattt ctagagg      57

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
ccggaagctt ttattcgtcg tgcgagatta tcg                              33

<210> SEQ ID NO 5
<211> LENGTH: 12
<212> TYPE: PRT
<213> ORGANISM: Artificial Sequence
<220> FEATURE:
<223> OTHER INFORMATION: synthetic oligopeptide

<400> SEQUENCE: 5

Met Ala Asp Trp Leu Thr Phe Gln Lys Lys His Ile
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: synthetic oligopeptide

<400> SEQUENCE: 6

Met Gln Asp Trp Leu Thr Phe Gln Lys Lys His Ile
 1               5                  10

<210> SEQ ID NO 7
<211> LENGTH: 4
<212> TYPE: PRT
<213> ORGANISM: Artificial Sequence
<220> FEATURE:
<223> OTHER INFORMATION: synthetic oligopeptide

<400> SEQUENCE: 7

Met Ala Asp Tyr
 1

<210> SEQ ID NO 8
<211> LENGTH: 6
<212> TYPE: PRT
<213> ORGANISM: Artificial Sequence
<220> FEATURE:
<223> OTHER INFORMATION: synthetic oligopeptide

<400> SEQUENCE: 8

Met Ala Asp Tyr Leu Thr
 1               5

<210> SEQ ID NO 9
<211> LENGTH: 6
<212> TYPE: PRT
<213> ORGANISM: Artificial Sequence
<220> FEATURE:
<223> OTHER INFORMATION: synthetic oligopeptide
```

```
<400> SEQUENCE: 9

Met Gln Asp Tyr Leu Thr
1               5

<210> SEQ ID NO 10
<211> LENGTH: 5
<212> TYPE: PRT
<213> ORGANISM: Escherichia coli

<400> SEQUENCE: 10

Met Gln Asp Trp Leu
1               5

<210> SEQ ID NO 11
<211> LENGTH: 5
<212> TYPE: PRT
<213> ORGANISM: Escherichia coli

<400> SEQUENCE: 11

Met Gln Asp Trp Glu
1               5

<210> SEQ ID NO 12
<211> LENGTH: 5
<212> TYPE: PRT
<213> ORGANISM: Escherichia coli

<400> SEQUENCE: 12

Met Gln Asp Trp Asp
1               5

<210> SEQ ID NO 13
<211> LENGTH: 5
<212> TYPE: PRT
<213> ORGANISM: Escherichia coli

<400> SEQUENCE: 13

Met Gln Asp Trp Ala
1               5

<210> SEQ ID NO 14
<211> LENGTH: 5
<212> TYPE: PRT
<213> ORGANISM: Escherichia coli

<400> SEQUENCE: 14

Met Gln Ala Trp Ala
1               5

<210> SEQ ID NO 15
<211> LENGTH: 5
<212> TYPE: PRT
<213> ORGANISM: Escherichia coli

<400> SEQUENCE: 15

Met Ala Ala Trp Ala
1               5

<210> SEQ ID NO 16
<211> LENGTH: 5
<212> TYPE: PRT
<213> ORGANISM: Escherichia coli

<400> SEQUENCE: 16
```

```
Met Ala Pro Trp Ala
1               5

<210> SEQ ID NO 17
<211> LENGTH: 5
<212> TYPE: PRT
<213> ORGANISM: Escherichia coli

<400> SEQUENCE: 17

Met Gln Asn Trp Glu
1               5

<210> SEQ ID NO 18
<211> LENGTH: 5
<212> TYPE: PRT
<213> ORGANISM: Escherichia coli

<400> SEQUENCE: 18

Met Gln Asn Trp Ala
1               5

<210> SEQ ID NO 19
<211> LENGTH: 5
<212> TYPE: PRT
<213> ORGANISM: Escherichia coli

<400> SEQUENCE: 19

Met Gln Asp Trp Ala
1               5

<210> SEQ ID NO 20
<211> LENGTH: 5
<212> TYPE: PRT
<213> ORGANISM: Escherichia coli

<400> SEQUENCE: 20

Met Leu Ala Gly Ala
1               5

<210> SEQ ID NO 21
<211> LENGTH: 5
<212> TYPE: PRT
<213> ORGANISM: Escherichia coli

<400> SEQUENCE: 21

Met Gln Asp Ile Leu
1               5
```

REMOVAL OF N-TERMINAL METHIONINE FROM PROTEINS BY ENGINEERED METHIONINE AMINOPEPTIDASE

TECHNICAL FIELD

This invention relates to methods and compositions useful for removing the N-terminal methionine from proteins, particularly methods employing engineered methionine aminopeptidases and compositions thereof.

REFERENCES

U.S. Pat. No. 5,013,662.

Abe, A., et al. (2000) Acetylation at the N-terminus of actin strengthens weak interaction between actin and myosin. Biochem. Biophys. Res. Commun., 268:14–19.

Adachi, K., et al. (2000) Expression of functional soluble human alpha-globin chains of hemoglobin in bacteria. Protein Expr. Purif., 20:37–44.

Belagaje, R. M., et al. (1997) Increased production of low molecular weight recombinant proteins in Escherichia coli. Protein Sci., 6:1953–1962.

Ben-Bassat, A., et al. (1987) Processing of the initiation methionine from proteins: properties of the Escherichia coli methionine aminopeptidase and its gene structure. J. Bacteriol., 169:751–757.

Boix, E., et al. (1996) Role of the N terminus in RNase A homologues: differences in catalytic activity, ribonuclease inhibitor interaction and cytotoxicity. J. Mol. Biol., 257:992–1007.

Busby, W. H., Jr., et al. (1987) An enzyme(s) that converts glutaminyl-peptides into pyroglutamyl-peptides. Presence in pituitary, brain, adrenal medulla, and lymphocytes. J. Biol. Chem., 262:8532–8536.

Chang, S. Y., et al. (1989) Methionine aminopeptidase gene of Escherichia coli is essential for cell growth. J. Bacteriol., 171:4071–4072.

Chen, S., et al. (2002) The specificity in vivo of two distinct methionine aminopeptidases in Saccharomyces cerevisiae. Arch. Biochem. Biophys., 398:87–93.

Chiu, C. H., et al. (1999) Amino acid residues involved in the functional integrity of Escherichia coli methionine aminopeptidase. J Bacteriol 181:4686–4689.

Endo, S., et al. (2001) The additional methionine residue at the N-terminus of bacterially expressed human interleukin-2 affects the interaction between the N- and C-termini. Biochemistry, 40:914–919.

Fischer, W. H., and Spiess, J. (1987) Identification of a mammalian glutaminyl cyclase converting glutaminyl into pyroglutamyl peptides. Proc. Natl. Acad. Sci. U.S.A., 84:3628–3632.

Hirel, P. H., et al. (1989) Extent of N-terminal methionine excision from Escherichia coli proteins is governed by the side-chain length of the penultimate amino acid. Proc. Natl. Acad. Sci. U.S.A., 86:8247–8251.

Huang, H. C., et al. (1998) The Rana catesbeiana rcr gene encoding a cytotoxic ribonuclease. Tissue distribution, cloning, purification, cytotoxicity, and active residues for RNase activity. J. Biol. Chem., 273:6395–6401.

Hwang, D. D., et al. (1999) Co-expression of glutathione S-transferase with methionine aminopeptidase: a system of producing enriched N-terminal processed proteins in Escherichia coli. Biochem. J., 338 (Pt 2):335–342.

Ishitani, M., et al. (2000) SOS3 function in plant salt tolerance requires N-myristoylation and calcium binding. Plant Cell, 12:1667–1678.

Leu, Y. J., et al. (2003) Residues involved in the catalysis, base specificity, and cytotoxicity of ribonuclease from Rana catesbeiana based upon mutagenesis and X-ray crystallography. J. Biol. Chem., 278:7300–7309.

Li, X., and Chang, Y. H. (1995) Amino-terminal protein processing in Saccharomyces cerevisiae is an essential function that requires two distinct methionine aminopeptidases. Proc. Natl. Acad. Sci. U.S.A., 92:12357–12361.

Liao, Y. D., and Wang, J. J. (1994). Yolk granules are the major compartment for bullfrog (Rana catesbeiana) oocyte-specific ribonuclease. Eur J. Biochem., 222:215–220.

Liao, Y. D., et al. (2000) Purification and cloning of cytotoxic ribonucleases from Rana catesbeiana (bullfrog). Nucleic Acids Res., 28:4097–4104.

Liao, Y. D., et al. (2003) The structural integrity exerted by N-terminal pyroglutamate is crucial for the cytotoxicity of frog ribonuclease from Rana pipiens. Nucleic Acids Res., 31:5247–5255.

Lowther, W. T., et al. (1999) Escherichia coli methionine aminopeptidase: implications of crystallographic analyses of the native, mutant, and inhibited enzymes for the mechanism of catalysis. Biochemistry, 38:7678–7688.

Lowther, W. T., and Matthews, B. W. (2000) Structure and function of the methionine aminopeptidases. Biochim. Biophys. Acta., 1477:157–167.

Moerschell, R. P., et al. (1990) The specificities of yeast methionine aminopeptidase and acetylation of amino-terminal methionine in vivo. Processing of altered iso-1-cytochromes c created by oligonucleotide transformation. J. Biol. Chem., 265:19638–19643.

Notomista, E., et al. (1999) Effective expression and purification of recombinant onconase, an antitumor protein. FEBS Lett., 463:211–215.

Prchal, J. T., et al. (1986) Hemoglobin Long Island is caused by a single mutation (adenine to cytosine) resulting in a failure to cleave amino-terminal methionine. Proc. Natl. Acad. Sci. U.S.A., 83:24–27.

Roderick, S. L., and Matthews, B. W. (1993) Structure of the cobalt-dependent methionine aminopeptidase from Escherichia coli: a new type of proteolytic enzyme. Biochemistry, 32:3907–3912.

Shapiro, R., et al. (1988) Expression of Met-(−1) angiogenin in Escherichia coli: conversion to the authentic less than Glu-1 protein. Anal. Biochem., 175:450–461.

Tahirov, T. H., et al. (1998) Crystal structure of methionine aminopeptidase from hyperthermophile, Pyrococcus furiosus. J. Mol. Biol., 284:101–124.

Tobias, J. W., et al. (1991) The N-end rule in bacteria. Science, 254:1374–1377.

Varshavsky, A. (1996) The N-end rule: functions, mysteries, uses. Proc. Natl. Acad. Sci. U.S.A., 93:12142–12149.

Vetro, J. A., and Chang, Y. H. (2002) Yeast methionine aminopeptidase type 1 is ribosome-associated and requires its N-terminal zinc finger domain for normal function in vivo. J. Cell. Biochem., 85:678–688.

Walker, K. W., and Bradshaw, R. A. (1999) Yeast methionine aminopeptidase I. Alteration of substrate specificity by site-directed mutagenesis. J. Biol. Chem., 274:13403–13409.

Wilkins, M. R., et al. (1998) Protein identification and analysis tools in the ExPASy Server. Humana Press, New Jersey.

All of the publications, patents and patent applications cited above or elsewhere in this application are herein incorporated by reference in their entirety to the same extent as if the disclosure of each individual publication, patent

BACKGROUND

Removal of the translation initiator N-formyl-methionine or methionine from a recombinant protein is often critical for its function and stability. For example, it has been shown that such removal is essential for human hemoglobin, interleukin-2, growth hormones or frog ribonucleases (Adachi et al., 2000; Endo et al., 2001; Busby et al., 1987; Liao et al., 2003; Boix et al., 1996; Varshavsky, 1996). For the preparation of proteins with innate N-terminus, various attempts have been made to remove the N-terminal Met. First, cyanogen bromide (CNBr) was used to cleave Met under extreme acidic conditions, but the method is limited to proteins without any internal Met residue (Boix et al., 1996). Second, a protease-specific oligopeptide was introduced in front of a target protein, which was then removed in vitro by the respective protease, e.g., factor Xa, enterokinase or cathepsin C (Belagaje et al., 1997). Third, the N-terminal Met of a protein was removed in vitro by the aminopeptidase of Aeromonas proteolytica (Notomista et al., 1999; Shapiro et al., 1988). Fourth, a signal peptide was introduced in front of target protein and processed in vivo during secretion, but the yield was low (1~5 mg per liter of culture) (Huang et al., 1998).

Recently, methionine aminopeptidases (MetAPs) were employed to remove the N-terminal Met in *E. coli* and yeast. There are two types of MetAP, MetAP I and MetAP II, in eukaryotes. Only MetAP I exists in eubacteria; MetAP II is present in archaea (Li et al., 1995; Tahirov et al., 1998). It has been demonstrated that the genes for these MetAPs are essential for the growth of prokaryotes and eukaryotes (Li et al., 1995; Chang et al., 1989). However, the efficiency of Met removal is limited by the size of the side chain (radius<3.68 Å) of the penultimate residue, the residue next to the N-terminal Met (Ben-Bassat et al., 1987; Hirel et al., 1989; Hwang et al., 1999; Chen et al., 2002). Thus, Met removal for proteins with larger or bulky penultimate residues is inefficient. It is also difficult to remove the N-terminal Met when the penultimate residue is charged, either acidic (Glu or Asp) or basic (Lys, Arg or His).

From the structure of *E. coli* MetAP and bestatin-based inhibitor complex, it was discovered that four residues (Tyr168, Gln233, Met206 and Glu204) reside in the substrate binding pocket (Lowther et al., 1999; Lowther et al., 2000). The Met329 and Gln356 residues of yeast MetAP, corresponding to Met206 and Gln233 of *E. coli* MetAP, were replaced with Ala. When tested in vitro, these purified MetAP I variants (M329A, Q356A) had significantly increased catalytic activities for oligopeptides with slightly larger penultimate residues, such as Asn, His and Met, but not with bulky or acidic penultimate residues (Roderick et al., 1993; Walker et al., 1999). Therefore, the need exists for a method to remove N-terminal Met that is more universally applicable, particularly a method that can remove the N-terminal Met from a bulky or acidic penultimate residue.

SUMMARY

The present invention provides methionine aminopeptidases (MetAPs) with a broad substrate range, particularly those capable of removing the N-terminal Met from bulky or acidic penultimate residues. In particular, these MetAPs have mutations at the 233, 206 and/or 168 positions of SEQ ID NO:1 (Accession No. GI146727). Preferably, amino acids at these residues are substituted with glycine or threonine. SEQ ID NO:1 is as follows:

```
MAISIKTPED IEKMRVAGRL AAEVLEMIEP YVKPGVSTGE

LDRICNDYIV NEQHAVSACL GYHGYPKSVC ISINEVVCHG

IPDDAKLLKD GDIVNIDVTV IKDGFHGDTS KMFIVGKPTI

MGERLCRITQ ESLYLALRMV KPGINLREIG AAIQKFVEAE

GFSVVREYCG HGIGRGFHEE PQVLHYDSRE TNVVLKPGMT

FTIEPMVNAG KKEIRTMKDG WTVKTKDRSL SAQYEHTIVV

TDNGCEILTL RKDDTIPAII SHDE
```

Accordingly, one aspect of the present invention provides a polypeptide comprising an engineered version of SEQ ID NO:1, wherein residue 206 or 233 of SEQ ID NO:1 is substituted with an amino acid selected from the group consisting of Gly, Thr, Asp, Val and Asn. Residue 233 is preferably substituted with Gly or Thr, and residue 206 is preferably substituted with Gly, Thr or Val. More preferably, both residues 206 and 233 are substituted. The preferred double mutants include the following substitutions:
  (a) residue 206 is substituted with Gly and residue 233 is substituted with Gly;
  (b) residue 206 is substituted with Thr and residue 233 is substituted with Gly;
  (c) residue 206 is substituted with Thr and residue 233 is substituted with Thr; or
  (d) residue 206 is substituted with Val and residue 233 is substituted with Thr.

Optionally, residue 168 is also substituted, preferably with an amino acid selected from the group consisting of Gly, Ser, Thr, Val, Asp and Glu, and more preferably with Gly or Thr.

Another aspect of the present invention provides a polypeptide comprising an engineered version of SEQ ID NO:1, wherein residues 168, 206 and/or 233 of SEQ ID NO:1 have been substituted, the polypeptide being capable of cleaving the amino terminal methionine from a substrate polypeptide wherein the amino acid next to the methionine in the substrate polypeptide is selected from the group consisting of His, Asn, Gln, Leu, Ile, Phe, Met, Glu and Asp.

Also provided are cells comprising the engineered polypeptides described in the present application. The cells may be eukaryotic or prokaryotic. Preferably, the cells are mammalian cells, insect cells (such as the High Five cells) or bacterial cells. The cells are more preferably *E. coli*.

Further provided are DNA molecules that encode the engineered polypeptides of the present invention, particularly expression vectors.

Another aspect of the present invention provides a method of removing the N-terminal methionine from a target protein, comprising contacting the target protein with the engineered polypeptides (MetAPs) of the present invention under conditions that result in removal of the N-terminal methionine from the target protein. For example, this method can be practiced by introducing a DNA that encodes the MetAP polypeptide into a cell, wherein the cell expresses the target protein. The method can also be practiced by introducing into a cell a DNA that encodes the MetAP polypeptide and a DNA that encodes the target protein.

Preferably, the amino acid residue next to the N-terminal methionine in the target protein is selected from the group consisting of Gln, Asn, Asp, Glu, Leu, Ile, Met and His. More preferably, this residue (the penultimate residue) is Glu or Asp.

A further aspect of the present invention provides compositions that comprise at least one of the engineered polypeptides (MetAPs) of the present invention, a DNA encoding the MetAP, or a cell comprising the MetAP.

Also provided are kits that can be used to remove the N-terminal Met from a target protein. The kits comprise at least two components selected from the group consisting of:

(1) at least one engineered MetAP as described herein or a nucleic acid encoding the MetAP;
(2) a cell comprising at least one engineered MetAP as described herein or a nucleic acid encoding the MetAP;
(3) a plasmid for expressing the target protein;
(4) a positive control protein that can be processed by the MetAP or a nucleic acid encoding the positive control protein;
(5) an instruction of use; and
(6) a container for the components of the kit.

Preferably, at least one component in the kit is (1), (2) or (3).

The details of one or more embodiments of the invention are set forth in the disclosure below. Other features, objects, and advantages of the invention will be apparent from the description, drawings, and claims.

Figure 1:
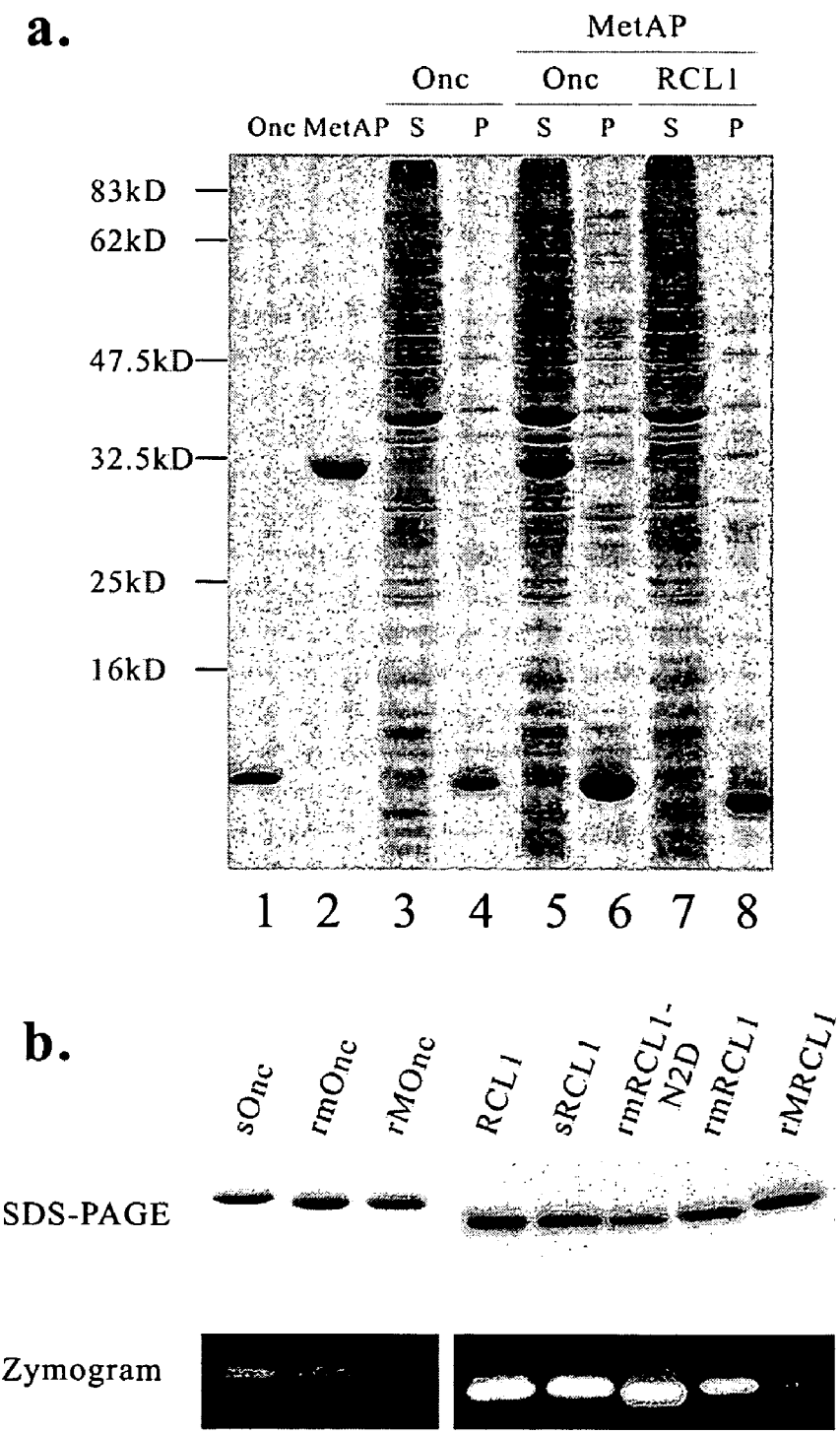
FIG. 1. Expression and analyses of MetAP and target ribonucleases.

(a). Co-expression of MetAP and target ribonucleases. The protein component of supernatant (S) and insoluble pellet (P) of 30 μl transformed E. coli BL21(DE3) culture was analyzed by 13.3% SDS-PAGE and Coomassie blue staining. Lane 1, 2 μg onconase; lane 2, 3 μg MetAP; lane 3, 4, supernatant and pellet of E. coli expressing onconase only; lane 5, 6, supernatant and pellet of E. coli co-expressing engineered MetAP and onconase; lane 7, 8, supernatant and pellet of E. coli co-expressing engineered MetAP and RC-RNaseL1.

(b). Analyses of recombinant ribonucleases. Top panel. 2 μg of purified ribonuclease was separated by 13.3% SDS-PAGE and stained by Coomassie blue. Bottom panel. 10 ng onconase and 1 ng RC-RNaseL1 were separated by RNA-casting SDS-PAGE and stained by Toluidine blue. sOnc and sRCL1 represent secretory onconase and RC-RNase L1, respectively, which were purified from culture medium; rmOnc, rmRCL1 and rmRCL1-N2D represent Met-tagged onconase, RC-RNase L1 and RC-RNase L1-N2D, respectively, which were treated with MetAP-*TG in vivo; rMOnc and rMRCL1 represent Met-tagged onconase and RC-RNase L1, respectively, without MetAP treatment; RCL1 represents native RC-RNase L1 purified from bullfrog liver.

DETAILED DESCRIPTION

The present invention provides methionine aminopeptidases (MetAPs) with a broad substrate range, particularly those capable of removing the N-terminal Met from bulky or acidic penultimate residues. In preferred embodiments, these MetAPs have mutations at the 233, 206 and/or 168 positions of SEQ ID NO:1. Preferably, amino acids at these residues are substituted with glycine or threonine.

Prior to describing the invention in further detail, the terms used in this application are defined as follows unless otherwise indicated.

DEFINITIONS

Domain: as used herein, domains of polypeptides are regions that possess a characteristic structure or function. Examples of domains include substrate binding domain, catalytic site, α-helices, β-sheets, β-bends, loops, and unstructured polypeptide regions between structured regions.

Engineered MetAP: a MetAP that has been modified by human maneuver. The engineered MetAP contains at least one amino acid that is different from the corresponding wild type MetAP, or the omission of at least one amino acid, when sequences of the wild type and the engineered version are aligned.

Expressing a polypeptide in a cell: causing the cell to produce, via protein translation, a polypeptide sequence of interest from a polynucleotide encoding such polypeptide.

Expression vector: a vector that encodes one or more polypeptides of interest along with appropriate transcriptional and translational regulatory sequences to allow expression of the polypeptide in a cell. Examples of expression vectors include plasmids, phages, and viruses. Expression vectors may comprise inducible or cell-type-specific promoters, enhancers or repressors, introns, polyadenylation signals, selectable markers, polylinkers, site-specific recombination sequences, and other features to improve functionality, convenience of use, and control over mRNA and/or protein expression levels, as known in the art.

Inducible promoter: a promoter that causes RNA to be transcribed from a particular polynucleotide sequence at different levels depending upon specific intracellular or environmental conditions. Inducible promoters may respond positively or negatively to, for example, the presence of hormones, nutrients, metabolites, toxins, stress, osmolarity, the activation or inactivation of certain cellular biochemical pathways, or other means of regulating gene expression.

Methionine aminopeptidase (MetAP): an enzyme that is capable of removing the methionine residue from the N-terminus of a protein.

Polypeptide: a molecule having any number of contiguous amino acid residues linked via peptide bonds. As used herein, polypeptide and protein are interchangeable terms.

Substantial sequence similarity: with respect to polypeptides, substantial sequence similarity exists when two polypeptide sequences are at least about 50%, at least about 60%, at least about 70%, at least about 80%, at least about 90%, or at least about 95% identical at the primary sequence level, as determined by a sequence alignment program available in the art, such as Clustal W.

Substantially more efficient: a MetAP is substantially more efficient than a second MetAP if the MetAP removes the N-terminal Met from a substrate at least about 50% more efficiently than the second MetAP. For example, if the MetAP can remove the N-terminal Met from about 25% of a substrate and the second MetAP removes the N-terminal Met from about 15% of the same substrate, the MetAP is substantially more efficient than the second MetAP. If the second MetAP cannot process a substrate, i.e., the level of Met removal is undetectable, then the MetAP is substantially more efficient than the second MetAP as long as the MetAP can remove the N-terminal Met from at least 1% of the same substrate. The MetAP is preferably at least about 100% more efficient, more preferably at least about 150% more efficient, even more preferably at least about 200% more efficient, and most preferably at least about 250% more efficient than the second MetAP.

Methods

In this invention, I mutated at least one of three residues, Tyr168, Met206 and Gln233, but not the catalytic Glu204 residue, of *E. coli* MetAP by site-directed mutagenesis. Using a co-expression system producing a target protein and engineered MetAPs via the same or separate vector, I was able to remove from the target protein the N-terminal Met from bulky or acidic penultimate residue, e.g., Met, His, Asp, Asn, Glu, Gln, Leu, Ile, Phe and Trp in *E. coli* without further in vitro chemical or enzymatic treatment (Boix et al., 1996; Walker et al., 1999). Thus, proteins possessing the innate sequences were successfully produced.

A good example is onconase, an antitumor ribonuclease from the frog Rana pipiens (Boix et al., 1996). The N-terminal pyroglutamate of onconase is critical for its structural integrity, catalytic activity and cytotoxicity (Liao et al., 2003). However, since the translation initiation codon codes for Met, the nascent translational product of onconase starts with MQD and does not have the correct structure or function. Thus, to produce a functional onconase, the N-terminal Met has to be removed post-translationally. In *E. coli*, however, the methionine aminopeptidase cannot remove the N-terminal Met from onconase because the penultimate residue, Gln, is too bulky.

In this invention, a variety of engineered MetAPs were co-expressed with onconase (open reading frame starting with MQD) in *E. coli*. While the wild type MetAP failed altogether to remove the N-terminal Met from onconase, when residue 233 of the MetAP was substituted with glycine or threonine, the mutant MetAP cleaved the N-terminal Met efficiently from onconase (Example 2). Similarly, when residue 206 of the MetAP was substituted with glycine, threonine or valine, removal of the N-terminal Met was achieved (Example 2). Mutation of both the 233 and 206 residues further enhanced the efficiency of Met removal (Example 2).

To determine the activities of the engineered MetAPs on other N-terminal sequences, a number of onconase sequences were constructed, each containing a different penultimate residue. These target sequences were co-expressed with different engineered MetAPs, and the N-terminus of the resulting onconase was analyzed. As shown in Table 1, the double mutant *TG, in which residue 206 was substituted with threonine and residue 233 with glycine, exhibited significant activities over a wide range of substrates. Notably, even the N-terminal Met next to acidic residues, Glu and Asp, can be cleaved with substantial efficiency (see MDD-Onc and MED-Once of Table 1). Furthermore, when the penultimate residue is His, a basic residue, 92% of the N-terminal Met was cleaved with high efficiency (see MHD-One of Table 1). The enzymes are relatively inefficient, however, when the penultimate position is occupied by Arg or Lys.

I discovered that if residue 168 is also substituted with a relatively small amino acid, the efficiency of Met removal can be further improved. For example, while both the wild type MetAP and the *TG mutant were inactive for MYD-One or MWD-One, the GTG mutant (G at residue 168, T at residue 206 and G at residue 233) had much higher activities (Table 1).

In addition to the penultimate residue, the antepenultimate residue also influences the removal of N-terminal Met. Therefore, I constructed substrates in which the antepenultimate residues were varied, and determined the effects of the engineered MetAPs (Example 5). As shown in Table 2, the MetAPs are capable of cleaving the N-terminal Met in most of the cases.

Accordingly, the MetAPs of the present invention can remove the N-terminal Met from a wide selection of proteins, including those having acidic or bulky residues at the penultimate or antepenultimate positions. In order to assess the usefulness of the engineered MetAPs in general, I examined the N-terminal sequences of all the proteins in the protein database. From the eukaryotic curated (NP) protein sequence entries of the NCBI RefSeq database (dated Jan. 7, 2003) using the SignalP program, 37.4% of 5298 secretory proteins possess a small residue at the N-termini and 58.5% of 17978 nonsecretory proteins possess a small penultimate residue. The N-terminal Met of these proteins may be processed by wild type MetAP. In contrast, based on the results obtained by using the engineered MetAPs, up to 84.5% of secretory proteins and 90.2% of nonsecretory proteins should be produced in authentic form using the method described herein.

The present invention thus provides engineered methionine aminopeptidases in which the Tyr, Met or Gln residues in the putative substrate-binding pocket is substituted. In particular, the engineered MetAP comprises SEQ ID NO:1 except that the residues at positions 168, 206 and/or 233 are substituted. The residues are preferably substituted with small amino acids, such as Gly, Val, Thr, Asp and Asn. The substituting amino acids are more preferably Gly, Val or Thr.

It should be noted that the engineered MetAPs may contain other mutations (amino acid deletions, additions or substitutions) in addition to those at position 168, 206 or 233. Preferably, these additional mutations reside in domains or residues of the MetAPs known to be unimportant for function. For example, the C59S, Y62F, Y65F or F177L mutations in the putative substrate-binding pocket do not reduce catalytic activity. On the other hand, residues known to be important for MetAP activities should not be mutated. For example, the C70S and W221L mutations in the putative substrate-binding pocket significantly reduce its catalytic activity (54% and 27% activity of the wild type, respectively). The D97A, D108A, H171L, E204V and E235V mutations in the cobalt-binding site almost destroy its catalytic activity (2~6% of the wild type; Chiu et al. 1999). Residues Glu204 and Glu235 of *E. coli* MetAP are involved in $Co^{++}$ metal binding and catalytic activity (Lowther et al., 1999).

The engineered MetAPs should have an amino acid sequence similarity with the wild type MetAP, outside of residues 168, 206 and 233, that is at least about 50%, at least about 60%, at least about 70%, at least about 80%, at least about 90%, or at least about 95% at the primary sequence level, as determined by a sequence alignment program available in the art. More preferably, the engineered MetAP has only a limited number (such as 1–5) of point mutations outside of the substrate binding domain or catalytic site.

In addition to Met removal, the modification of N-terminal residue is often crucial for the function of protein. For example, the acetylation of N-terminal residue of actin strengthens its interaction with myosin (Abe et al., 2000) and the N-myristoylation of N-terminal Gly of SOS3 protein is essential for the salt tolerance of plants (Ishitani et al., 2000). The conversion of N-terminal glutamine to pyroglutamate (Pyr) is found at all known cytotoxic frog ribonucleases, some mammalian ribonucleases, immunoglobulins and hormones (thyrotropin releasing hormone, luteining hormone releasing hormone, gonadotropin-releasing hormone, corticotropin-releasing hormone and gastrin) (Busby et al., 1987; Liao et al., 2003; Boix et al., 1996; Fischer et al., 1987). Three hydrogen bonds exerted by N-terminal Pyr are essential for the structural integrity, catalytic activity and cytotoxicity of frog ribonucleases (Liao et al., 2003; Huang et al., 1998; Leu et al., 2003). In this invention, a large amount of de-methioninylated proteins (10~50 mg from one liter of culture) was prepared in vivo by engineered MetAP and the terminal Gln was converted to Pyr in vitro under mild conditions, instead of chemical and enzymatic treatments (Liao et al, 2003; Notomista et al, 1999; Shapiro et al., 1988). To prevent the subsequent cleavage of penultimate residue, the antepenultimate residue may be replaced with bulky or acidic residue if it does not alter the properties of the protein. Thus, the engineered MetAP and the expression system described herein are useful for the production of large quantities of soluble or insoluble proteins in authentic forms.

Also provided are engineered methionine aminopeptidase derived from wild type MetAPs that have sequences other than SEQ ID NO:1. In these cases, the sequence of the wild type enzyme is aligned with SEQ ID NO:1, and residues of the wild type enzyme that correspond to residues 168, 206 and/or 233 of SEQ ID NO:1 are mutated in the same fashion as described for SEQ ID NO:1. The engineered MetAP of the present invention should be capable of cleaving at least one substrate that cannot be processed by the corresponding wild type enzyme, or cleaving a substrate substantially more efficiently than the wild type enzyme. The wild type enzyme is preferably not the yeast MetAP.

The present invention also provides methods of producing or expressing proteins that do not have a N-terminal Met residue. This can be achieved by contacting a protein that has an N-terminal Met with a MetAP of this invention in vivo or in vitro. Preferably, the protein is expressed in a cell that also expresses an engineered MetAP. The protein and the engineered MetAP can be encoded by the same piece of DNA, such as a plasmid encoding both. Alternatively, the cell may have a gene encoding the MetAP integrated in its genome while the protein is expressed from a plasmid. The MetAP and the protein may also be encoded by two different plasmids.

Numerous methods of introducing polypeptides into cells are known in the art, including but not limited to transfection, microinjection, scrape-loading, and receptor-mediated uptake by the cells. Transfection may be transient or stable. Exemplary current methods of transfection include calcium phosphate precipitation, electroporation, lipofection, and peptide-mediated transfection. Ballistic DNA delivery and transduction (i.e., the introduction of foreign DNA by virus or virus vector infection) can also be employed.

For example, polypeptides of the present invention can be delivered to cells by means of an expression vector. Suitable expression vectors comprise a promoter that is active in the cells of interest. Expression vectors useful for practicing the invention may also include selectable markers, cell-type or cell-cycle-specific enhancers or repressors, polylinkers, start codons, ribosome binding sites, internal ribosome entry sites, introns, stop codons, polyadenylation signals, or other features that facilitate cloning and vector stability, mRNA stability and localization in the cell, translation efficiency, or combinations thereof.

Compositions

The present invention provides compositions that comprise at least one engineered MetAP as described herein or a nucleic acid encoding the MetAP. The nucleic acid may further comprise a "cassette" that can be used to express a substrate protein by inserting a sequence encoding the substrate protein into the cassette. The cassette preferably contains a promoter suitable for the host cell in which the MetAP and substrate protein are to be expressed. The cassette may optionally contain enhancers or other regulatory sequences suitable for the host cell. A multiple cloning site is preferably included in the cassette to facilitate insertion of a variety of substrate proteins.

The present invention also provides cells that comprise at least one engineered MetAP as described herein or a nucleic acid encoding the MetAP. The cell may be a prokaryotic or eukaryotic cell, preferably a prokaryotic cell, more preferably a bacterial cell, and most preferably an $E.$ $coli$. The cell may be in any form of culture, such as frozen, suspended in liquid medium, streaked on solid medium, or attached to a solid support. When harboring the nucleic acid encoding the MetAP, the nucleic acid may be integrated in the genome of the cell or present extra-chromosomally. The cell may further comprise a substrate protein or a nucleic acid encoding the substrate protein.

Kits

The present invention provides kits that can be used to remove the N-terminal Met from a target protein. The kits comprise at least two components selected from the group consisting of:

(1) at least one engineered MetAP as described herein or a nucleic acid encoding the MetAP;
(2) a cell comprising at least one engineered MetAP as described herein or a nucleic acid encoding the MetAP;
(3) a plasmid for expressing the target protein;
(4) a positive control protein that can be processed by the MetAP or a nucleic acid encoding the positive control protein;
(5) an instruction of use; and
(6) a container for the components of the kit.

The plasmid preferably comprises a "cassette" that can be used to express the target protein by inserting a sequence encoding the target protein into the cassette. The cassette preferably contains a promoter suitable for the host cell in which the MetAP and target protein are to be expressed. The cassette may optionally contain enhancers or other regulatory sequences suitable for the host cell. A multiple cloning site is preferably included in the cassette to facilitate insertion of a variety of target proteins. The plasmid may optionally comprise the coding sequence for the MetAP, thereby comprising both components (1) and (3).

Preferably, at least one component of the kit is (1), (2) or (3). A preferred embodiment of the kit comprises components (2) and (3), and optionally means for introducing (3) into (2). For example, the kit may comprise reagents for calcium phosphate-based transfection, electroporation, lipofection, or microinjection.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| ° C. = | degree Celsius |
| hr = | hour |
| min = | minute |
| sec = | second |
| µM = | micromolar |
| mM = | millimolar |

-continued

| | |
|---|---|
| M = | molar |
| ml = | milliliter |
| µl = | microliter |
| mg = | milligram |
| µg = | microgram |
| MetAP = | methionine aminopeptidase |
| DMEM = | Dulbecco's modified Eagle's medium |
| FBS = | fetal bovine serum |
| PBS = | phosphate buffered saline |
| PAGE = | polyacrylamide gel electrophoresis |
| Pyr = | pyroglutamate |

Materials and Methods

Construction of Expression Plasmids

The rpr (AF332139) gene encoding for the target protein, onconase, from Rana pipiens was tagged with NdeI and BamHI site at the 5' and 3' end, respectively, and inserted downstream of T7 promoter in the expression vector pET22b (Novagen) (Liao et al., 2003; Huang et al., 1998; Liao et al., 2000). The other target proteins were also cloned by the same method, including RC-RNase L1 (AF288642.2), RC-RNase 2 (AF242553), RC-RNase 3 (AF242554), RC-RNase 4 (AF242555), RC-RNase6 (AF242556) from Rana catesbeiana, CA150 (a transcription elongation regulator 1; NM_006706) and glutathione S-transferase (M14654).

The Escherichia coli methionine aminopeptidase gene (Accession Number M 15106) or its mutant was fused with the T7 promoter by three steps of PCR and inserted into the same pET22b vector containing a target protein, as described above, through SacI and HindIII. The first PCR was performed using oligonucleotide 1 (5'CGCGGAGCTC-GATCCCGCGAAATTAATACG3'; SEQ ID NO:2) and oligonucleotide 2 (5'CTTGATTGAGATAGCCATTATCTC-CTTCTTAAAGTTAAACAAAATTATTTCTAGA GG3'; SEQ ID NO:3) as 5' and 3' primer, respectively, and pET22b as template. The second PCR was performed using the PCR product from step 1 as 5' megaprimer, oligonucleotide 3 (5'CCGGAAGCTTTTATTCGTCGTGCGAGATTATCG3'; SEQ ID NO:4) as 3' primer, and the E. coli MetAP gene (M15101) as template (Huang et al., 1998; Ben-Bassat et al., 1987). The third PCR was to amplify the second PCR product using oligonucleotide 1 and oligonucleotide 3 as primers. The genes encoding the target protein and E. coli MetAP have their own T7 RNA polymerase promoter, but they may be transcribed into the same RNA molecule for cotranslation because only one transcription terminator exists, downstream of the MetAP gene. Alternatively, the MetAP gene alone may be directly subcloned into vector pET29b through the SacI and HindIII site.

Residues Tyr168, Met206 and Gln233 in the putative substrate-binding site of E. coli MetAP were mutated by site-directed mutagenesis based on the crystal structure and amino acid sequence alignment of MetAPs (Ben-Bassat et al., 1987; Lowther et al., 1999; Walker et al., 1999). For the expression of secretory ribonucleases, the ribonuclease gene was cloned and expressed as described previously (Huang et al., 1998).

Expression and Purification of MetAP and Target Proteins

The MetAP was expressed alone or co-expressed with a target protein, i.e., onconase and RC-RNaseL1, in E. coli BL21 (DE3) in the presence of 0.5 mM IPTG at 37° C. After sonication, the MetAP in soluble fraction was dialyzed against buffer A (20 mM Hepes, pH 8.0, 50 mM KCl) and purified to homogeneity by phosphocellulose (Whatman P-11) and DEAE-cellulose (Whatman DE52) column chromatography at a yield of 50 mg per 1 liter of culture.

Most of the co-expressed target protein, e.g., onconase or RC-RNase L1, existed in insoluble cell lysate. They were denatured, renatured and purified as described previously (Liao et al., 2003). The purified ribonucleases were stored in 20 mM sodium phosphate, pH 7.0, for pyroglutamate formation at the N-terminus. Alternatively, the ribonuclease secreted into culture medium through pelB system was concentrated and purified to electrophoretical homogeneity at a yield of 1~5 mg per 1 liter of culture (Huang et al., 1998).

Analysis of N-Termini of Recombinant Proteins

Proteins in the cell pellet or in the soluble fraction were separated by 13.3% SDS-PAGE and contact-transferred to ProBlott™ membrane (Applied Bioystems) in transfer buffer (10 mM Tris-HCl, pH 7.5, 50 mM NaCl, 2 mM EDTA, 0.5 mM 2-mercaptoethanol) overnight. The five N-terminal residues of the transferred protein were determined by Edman degradation. The percentage of Met removal was calculated by dividing the amount of proteins initiated with the penultimate residue with the amount of total proteins (including proteins initiated with the penultimate residue and unprocessed protein initiated with Met) after the first degradation cycle. In theory, this percentage should remain the same after each degradation cycle. Therefore, in order to avoid experimental variation, the same calculation was made from five consecutive degradation cycles, e.g., M, Q, N, W and L for onconase. The efficiency of Met removal is reported as the mean values of at least three cycles. The mass spectrum analysis was carried out as described previously (Liao et al., 2003).

In Vitro MetAP Activity Assay

The oligopeptide substrates used in this experiment were synthesized on the 432A Synergy peptide synthesizer (Applied Biosystems, Foster, Calif., USA). The enzymatic activity of purified MetAP was assayed as described by Ben-Bassat et al., 1987. Briefly, the diluted MetAP enzyme in 10 µl was added to 90 µl of the substrate solution containing 4 mM oligopeptide, 0.1 M potassium phosphate buffer, pH 7.5 and 0.2 mM $CoCl_2$, incubated at 37° C. for 10 min and stopped in boiling water for 2 min. After addition of 0.9 ml of color development mixture containing 0.2 mg of L-amino acid oxidase, 0.03 mg of horseradish peroxidase and 0.2 mg of o-dianisidine in 0.1 M Tris-HCl, pH 7.4, the mixtures were incubated for 10 min at 37° C., and the optical density at 440 nm was recorded. One unit of activity is defined as 1 µmol of amino acids produced per min under the assay conditions and the pure Met was used as standard. The N-terminal residues of the MetAP-treated oligopeptide were further verified by Edman degradation.

Ribonuclease Activity Assay

Ribonuclease activity was analyzed by zymogram assay on RNA-casting PAGE (Liao and Wang, 1994). In addition, the ribonuclease activity of each purified ribonuclease was determined by the release of acid-soluble nucleotides from bakers' yeast total RNA after ribonuclease digestion. One unit of enzyme activity was defined as the amount of enzyme producing one A260 acid-soluble material at 37° C. for 15 min (Huang et al., 1998).

Example 1

Production of MetAP and Target Proteins

The genes encoding engineered MetAPs were expressed alone or co-expressed with a target protein in E. coli BL21 (DE3). The MetAP was soluble (FIG. 1a, lanes 5 and 7) and purified to electrophoretical homogeneity (lane 2). The yields of MetAP varied with the type of co-expressed target protein, e.g., 50 mg purified protein was obtained per 1 liter of culture in the absence of target proteins. The solubility and yield of co-expressed target proteins varied with the nature of the target proteins and condition of culture. For example, frog ribonuclease, (e.g., onconase or RC-RNaseL1) was insoluble at 37° C. culture (FIG. 1a, lanes 4, 6 and 8), while the whole CA150 protein (a transcription elongation regulator) was soluble. Glutathione S-transferase (GST) was partially soluble.

Example 2

Residues 233 and 206 are Involved in Substrate Specificity

Residue Gln233 is adjacent to two Co$^{++}$ ions and two catalytic residues, Glu204 and Glu235, in the substrate-binding pocket of E. coli MetAP. To determine the importance of residue 233 in the substrate specificity of MetAP, the Gln residue at 233 was replaced by a small amino acid, e.g., Gly, Thr, Asp or Asn. The resulting MetAPs are designated MetAP-Q233G, MetAP-Q233T, MetAP-Q233D, and MetAP-Q233N, respectively. Each MetAP mutant was co-expressed with the target protein, the onconase which begins with MQD (MQD-One). The N-terminal residue of the co-expressed onconase was then determined as described in Materials and Methods. The results show that the Met preceding Gln was removed by MetAP-Q233G (74% of Met removal) and MetAP-Q233T (88%). In contrast, the wild type enzyme had no activity.

A second residue, Met206, which is close to the catalytic residue His79 (2.97 Å), was replaced by a small amino acid, e.g., Gly, Thr or Val. The resulting MetAPs are designated MetAP-M206G, MetAP-M206T, and MetAP-M206V, respectively. Upon co-expression of MQD-One with the MetAP mutants, the N-terminal methionine of MQD-One was removed by MetAP-M206G (85% of Met removal), MetAP-M206T (86%) and MetAP-M206V (61%).

Double mutations were then prepared at positions Met206 and Gln233 to test the effects of double mutations, and the results are shown in Table 1. For the substrate MQD-Onc, the double mutants MetAP-M206G-Q233G (96%), MetAP-M206T-Q233G (91%), MetAP-M206T-Q233T (93%) and MetAP-M206V-Q233T (90%) displayed high catalytic activities. These mutants are designated as MetAP-*GG; MetAP-*TG; MetAP-*TT, MetAP-*VT, respectively, in Table 1.

TABLE 1

The effect of penultimate residue of substrate on the in vivo catalytic activity of engineered MetAPs

| Substrate | Catalytic activity (%)[a] | | | | Max. side chain length (Å)[c] |
|---|---|---|---|---|---|
| | MetAP-YMQ[b] | MetAP-*TG | MetAP-GTG | MetAP-TTG | |
| M↓GD-Onc[d] | 100[e] | 95 | | | 0.00 |
| M↓AD-Onc | 100 | 99 | | | 1.51 |
| M↓PD-Onc | 80–90 | 93 | | | 2.40 |
| M↓SD-Onc | 80–90 | 99 | | | 2.41 |
| M↓TD-Onc | 80–90 | 85 | | | 2.54 |
| M↓VD-Onc | 80–90 | 80 | | | 2.55 |
| M↓ND-Onc | ~20 | 85 | | | 3.68 |
| M↓DD-Onc | ~20 | 68 | 27 | 80 | 3.74 |
| M↓LD-Onc | ~20 | 86 | 90 | | 3.90 |
| M↓ID-Onc | ~20 | 22 | 94 | 68 | 3.91 |
| M↓HD-Onc | 0 | 92 | | | 4.64 |
| M↓QD-Onc | 0 | 91 | 97 | | 4.93 |
| M↓ED-Onc | 0 | 33 | 35 | 58 | 4.97 |
| M↓FD-Onc | 0 | 5 | 23 | | 5.10 |
| M↓M↓D-Onc | 0 | 100(73)[e] | | | 5.46 |
| M↓KD-Onc | 0 | 3 | 7 | | 6.37 |
| M↓YD-Onc | 0 | 1 | 20 | | 6.43 |
| M↓WD-Onc | 0 | 2 | 78 | | 6.64 |
| M↓RD-Onc | 0 | 2 | 4 | | 7.40 |

[a]Activity was expressed by percentage of the removal of terminal residue from Met-tagged onconase with different penultimate residue.
[b]MetAP-YMQ represents the wild type E. coli Met aminopeptidase.
[c]The information of maximal side chain length of amino acid residue and the efficiency of Met removal by wild type MetAP were adapted from the results of Hirel et al., 1989.
[d]The vertical arrow represents the site cleaved by MetAP.
[e]The value in parenthesis represents the percent of penultimate residue which is removed by MetAP.

Example 3

Residue 168 is Also Involved in Substrate Specificity

A third residue, Tyr168, which forms a hydrogen bond with the catalytic His79 residue in the substrate-binding pocket of MetAP, was further replaced in MetAP-*TG with a small residue, Gly, Ser, Thr, Val, Asp or Glu. These triple mutants are designated as MetAP-GTG, MetAP-STG, MetAP-TTG MetAP-VTG, MetAP-DTG and MetAP-ETG, respectively. For the substrate MID-One, the efficiency of Met removal by the parent enzyme, MetAP-*TG, was 22%. The efficiency increased markedly to 94% by the Y168G mutation and 68% by the Y168T mutation (MetAP-GTG and MetAP-TTG; respectively, in Table 1).

Interestingly, for substrates with acidic penultimate residues, e.g., MDD-One or MED-One, the Y168T mutation exerted higher activity than that of Y168G mutation (Table 1). The result suggests that the hydroxyl group of residue 168 of E. Coli MetAP with shorter side chain may play a crucial role in the recognition of acidic penultimate residue.

Example 4

Effect of the Penultimate Residue on Substrate Specificity

To determine the effect of the penultimate residue, namely the residue next to the N-terminal methionine, on removal of the N-terminal methionine, MXD-One was used as substrate which possesses different penultimate residue (Table 1). The results indicate that MetAP-*TG exerted high catalytic activity on a variety of substrates, such as MLD-Onc (86% Met removal), MND (85%), MDD (68%), MHD (92%), MQD (91%) and MMD-Onc (100% for removal of the first Met and 73% for removal of the second Met) (Table 1). Strangely, MetAP-*GG had high catalytic activity only for MQD-One (96%), but low activity for MLD-Onc (18%) and MID-One (5%) despite the apparent large pocket for substrate. In contrast, the wild type enzyme had only negligible activities on these substrates.

Thus, the Met preceding moderate penultimate residues, i.e., Asn (85%), Leu (86%), His (92%), Gln (90%) and Met (100%), as well as small and uncharged residue, i.e., Gly (95%), Ala (99%), Pro (93%), Ser (99%), Thr (85%) and Val (80%), was mostly removed by the MetAP-*TG For proteins with bulky penultimate residue, Ile and Trp, most of the N-terminal Met was removed by MetAP-GTG (94% and 78%, respectively). It is noteworthy that MetAP-*TG even processed the N-terminal Met from acidic penultimate residues efficiently (68% for MDD-One and 33% for MED-One). While MetAP-*TG removed the N-terminal Met from His, a basic residue, with high efficiency (92%), the Met preceding the other basic penultimate residues, Lys and Arg, was hardly removable by these mutants.

These results thus show that the Met of most recombinant proteins is removed if the penultimate residue is bulky, even acidic or hydrophobic. However, the efficiency of Met removal from basic penultimate residue is still low, e.g., Lys (9% Met removal, see Table 2) and Arg (8%, see Table 2). The resistance of MK- or MR-initiated proteins to the engineered MetAP may be due to the charge repulsion and stereo hindrance of the substrate in the putative substrate-binding pocket of MetAP, e.g., His63, Met112, Asn95 and Trp221. Thus, it is contemplated that substitution of these charged and bulky residues with small or hydrophilic residues may improve the substrate recognition and catalytic activity of MetAP.

Example 5

Effect of the Antepenultimate Residue on Substrate Specificity

In addition to penultimate residue, the antepenultimate residue may play a role in the MetAP activity. The catalytic activity of human or yeast MetAP was reduced when the penultimate Val/Thr residue was followed by Pro, e.g., the MVP-initiated human β-globin (Prchal et al., 1986) and MVP- or MTP-initiated yeast iso-1-cytochrome c (Moerschell et al., 1990). In contrast, both terminal Met and penultimate Ala residues were removable by E. coli MetAP when the antepenultimate residue was Pro, e.g., MAP-initiated human interleukin-2 (Ben-Bassat et al., 1987). It was speculated that other aminopeptidase(s) are responsible for the removal of penultimate Ala residue in vivo (Ben-Bassat et al., 1987).

In this study, the effects of the antepenultimate residues were determined using onconase starting with MAX, MLX, MQX or MXA.

Using MAX-Onc as substrate, the removal of terminal Met was not significantly altered by the change of antepenultimate residue. As shown in Table 2, the N-terminal Met was removed when the antepenultimate residue was small, moderate, acidic, or basic. However, the penultimate Ala was removable by the MetAPs only when the antepenultimate residue was small, i.e., Gly or Ala (Table 2). This result is consistent with the observation that the wild type MetAP could remove the N-terminal Met and penultimate Ala of MAA- or MAG-initiated onconase and RC-RNase 4 substrates (Tables 2 and 3).

Using MLX-One or MQX-One as substrate, the terminal Met and penultimate Leu/Gln residues were also removable by the MetAPs when the antepenultimate residue was small or moderate (such as Gly, Ala, Ser, Thr, Val, Asn), but not when the antepenultimate residue was bulky or charged (such as Asp, Glu, Phe, Trp, Lys or Arg). When the substrate was MFX-One or MWX-Onc, both the Met and Phe/Trp residues were removable by MetAP-GTG if the antepenultimate residue was Ala, but not when the antepenultimate residue was Asp (Table 2).

The removal of N-terminal Met from penultimate Ala/Leu/Gln residue by MetAP-*TG was reduced when the antepenultimate residue is Pro. In contrast, most of the newly exposed Leu/Gln residue preceding Pro was removed by MetAP-GTG, although only half of the N-terminal Met was removed (Table 2). The result suggests that the Pro residue at the antepenultimate site may exert a stereo hindrance on the catalytic activity of MetAP enzyme.

These results show that the N-terminal Met and penultimate Ala/Leu/Gln/Phe/Trp residue were removed in vivo in the presence of engineered MetAP when the antepenultimate residue is small. The terminal Met and penultimate Ala of MAA-initiated onconase or RC-RNase 4 were also removed by the wild type E. coli MetAP (Table 2 and Table 3). Once the terminal Met is removed by MetAP variants, the small antepenultimate residue should serve as a penultimate residue and enables the demethioninylated protein to be a suitable substrate for the subsequent cleavage of new terminal residue by MetAP. Thus, it is contemplated that the E. coli MetAP may possess other aminopeptidase activities for the terminal Ala, Leu, Gln, Phe and Trp. If this is true, other proteases would not be required, as suggested by Ben-Bassat et al. (Ben-Bassat et al., 1987).

The removal of N-terminal bulky residue, such as Leu, Gln, Phe and Trp, and exposure of small residues, such as Ala, Ser and Thr, may protect proteins from degradation because proteins possessing bulky N-terminal residue, known as destabilizing residues, have short half-lives and proteins possessing small terminal residues, known as stabilizing residues, have long half-lives, as predicted from the N-end rule of protein stability (Varshavsky, 1996; Tobias et al., 1991).

TABLE 2

Effect of antepenultimate residue of substrate on the in vivo catalytic activity of engineered MetAPs

| Substrate | Catalytic activity (%)[a] | | | Substrate | Catalytic activity (%) | |
| --- | --- | --- | --- | --- | --- | --- |
| | MetAP-YMQ[b] | MetAP-*TG | MetAP-GTG | | MetAP-*TG | MetAP-GTG |
| M↓A↓G-Onc[c] | 80(63)[d] | 80(57) | 86(16) | M↓L↓L-Onc | 88(24) | 93(55) |
| M↓A↓A-Onc | 85(77) | 100(25) | 100(30) | M↓L↓H-Onc | 75(36) | 100(51) |
| M↓A↓P-Onc | —[e] | 72(38) | N.D.[f] | M↓LM-Onc | 100 | 100 |

TABLE 2-continued

Effect of antepenultimate residue of substrate on the in vivo catalytic activity of engineered MetAPs

| Substrate | Catalytic activity (%)[a] | | | Substrate | Catalytic activity (%) | |
|---|---|---|---|---|---|---|
| | MetAP-YMQ[b] | MetAP-*TG | MetAP-GTG | | MetAP-*TG | MetAP-GTG |
| M↓AV-Onc | — | 100 | — | | | |
| M↓AN-Onc | — | 100 | — | M↓Q↓A-Onc | 100(100) | N.D.[f] |
| M↓AD-Onc | — | 100 | — | M↓Q↓P-Onc | 25 | 54(100) |
| M↓AL-Onc | — | 100 | 100 | M↓Q↓T-Onc | 76(26) | 86(79) |
| M↓AQ-Onc | — | 97 | — | M↓Q↓N-Onc | 100(65) | 83(90) |
| M↓AE-Onc | — | 96 | — | M↓QD-Onc | 91 | 97 |
| M↓AF-Onc | — | 100 | — | M↓QE-Onc | 71 | — |
| M↓AM-Onc | — | 96 | 96 | M↓QF-Onc | 80 | — |
| M↓AK-Onc | — | 100 | — | M↓Q↓M↓-Onc | 100(59) | 100, 100(73) |
| M↓AR-Onc | — | 94 | — | M↓QK-Onc | 78 | — |
| | | | | M↓QW-Onc | 95 | — |
| M↓L↓G-Onc | — | 100(100) | 87(46) | M↓QR-Onc | 83 | — |
| M↓L↓A-Onc | — | 100(100) | 100(80) | | | |
| M↓L↓P-Onc | — | 5 | 55(95) | M↓IA-Onc | 36 | 96 |
| M↓L↓S-Onc | — | 82(59) | 87(69) | M↓F↓A-Onc | 2 | 36(100) |
| M↓L↓T-Onc | — | 91 | 72(54) | M↓KA-Onc | 2 | 9 |
| M↓L↓V-Onc | — | 76(27) | 97(69) | M↓YA-Onc | 8 | 22 |
| M↓L↓N-Onc | — | 92(58) | 100(68) | M↓W↓A-Onc | 2 | 100(89) |
| M↓LD-Onc | — | 90 | 98 | M↓RA-Onc | 2 | 8 |

[a]Activity was expressed by percentage of the removal of terminal residue from Met-tagged onconase with different penultimate and antepenultimate residue.
[b]MetAP-YMQ represents the wild type E. coli Met aminopeptidase.
[c]The vertical arrow represents the site cleaved by MetAP.
[d]The value in parenthesis represents the percent of penultimate residue which is removed.
[e]the result was not done.
[f]N.D. indicates that no protein is detectable under the same culture condition.

TABLE 3

The substrate specificity of MetAP-*TG in Escherichia coli

| Substrate[a] | Solubility | Catalytic activity (%) |
|---|---|---|
| M↓QDWL (SEQ ID NO:10)-Onc | − | 91 |
| M↓QDWL (SEQ ID NO:10)-Onc[b] | − | 80 |
| M↓QDWE (SEQ ID NO:11)-RC3 | − | 96 |
| M↓QDWD (SEQ ID NO:12)-RC6 | − | 82 |
| M↓QDWA (SEQ ID NO:13)-RC4 | − | 93 |
| M↓Q↓AWA (SEQ ID NO:14)-RC4 | − | 100 (100)[c] |
| M↓A↓AWA (SEQ ID NO:15)-RC4 | − | 100 (18) |
| M↓A↓PWA (SEQ ID NO:16)-RC4 | − | 79 (63) |
| M↓Q↓NEW (SEQ ID NO:17)-RC2 | − | 80 (56) |
| M↓Q↓NWA (SEQ ID NO:18)-RCL1 | − | 96 (62) |
| M↓QDWA (SEQ ID NO:19)-RCL1 | − | 99 |
| M↓L↓AGA (SEQ ID NO:20)-CA150 | + | 100 (71) |
| M↓QDIL (SEQ ID NO:21)-GST | + | 87 |
| M↓QDIL (SEQ ID NO:21)-GST[b] | + | 71 |
| M↓QDIL (SEQ ID NO:21)-GST | − | 85 |
| M↓QDIL (SEQ ID NO:21)-GST[b] | − | 70 |

[a]Onc, onconase (AF332139); RC2, RC-RNase2 (AF242553); RC3, RC-RNase3 (AF242554); RC4, RC-RNase4 (AF242555); RC6, RC-RNase6 (AF242556); RCL1, RC-RNaseL1 (AF288642); CA150, a transcription elongation regulator 1 (NM_006706); GST, glutathione S-transferase (M14654).
[b]The gene of target protein was cloned in pET22b and co-transformed with MetAP-*TG which was cloned in pET29b. The expressions of both genes were driven by T7 RNA polymerase simultaneously.
[c]The value in parenthesis represents the percent of penultimate residue which is removed.

Example 6

Applications for Other Recombinant Proteins

To investigate the utility of engineered MetAPs in the production of other recombinant proteins, several soluble or insoluble proteins were employed as substrates. The N-terminal Met of insoluble MQD-initiated bullfrog ribonucleases (RC-RNase 3, RC-RNase 4, RC-RNase 6 and RC-RNase L1-N2D) was removed by MetAP-*TG; while both Met and Gln of insoluble MQN-initiated bullfrog ribonucleases (RC-RNase 2 and RC-RNase L1) were removed by the same enzyme (Table 3). The terminal Met of soluble or insoluble MQD-initiated glutathione S-transferase (GST) of Schistosoma japonicum was also removable by the MetAP-*TG Both Met and Leu of the soluble MLA-initiated CA150 protein, a transcription elongation regulator, were also removable (Table 3).

The MetAP target protein could be expressed from separate vectors. The MetAP-*TG gene was cloned in the vector pET29b, which has a kanamycin-resistance marker, while the gene of the target protein, e.g., onconase or GST, was cloned in a separate expression vector pET22b, which has an ampicilin resistance marker. The vectors were co-expressed in the E. coli BL21 (DE3). The Met of these two MQD-initiated proteins was also removable, but with a slightly lower efficiency (10–15% less) (Table 3). This reduction may be due to a lower copy number of the plasmid (and RNA transcript) encoding the engineered MetAP.

Example 7

Properties of Recombinant Ribonucleases Produced by the Present Method

N-Terminus:

The N-terminus of MetAP-processed MQD-initiated onconase was Gln as determined by Edman degradation, but it became a mixture of Gln/pyroglutamate soon after refolding from inclusion bodies from the mass spectrum analysis. Thus, one peak in the mass spectrum (11,818 Daltons) agreed with the mass of pyroglutamate-initiated native onconase, and the other (11,835 Daltons) agreed with that of Gln-initiated onconase as calculated by ExPASY server from the DNA sequence (Wilkins et al., 1998). The reduction of 17 Daltons indicates that pyroglutamate is derived from Gln through deamination. Similar results were also observed for the recombinant RC-RNase L1 proteins.

Catalytic Activity:

The catalytic activity of onconase was markedly reduced by the addition of Met and disruption of pyroglutamate at the N-terminus (100-fold less). To determine the activity of the onconase produced by the present invention, recombinant onconase expressed in the presence (rmOnc) or absence (rMOnc) of MetAP-*TG was assayed using the zymogram or acid-insoluble method. The results show that the catalytic activity of rmOnc was at a level similar to that of the native onconase isolated from frog oocyte, or the recombinant onconase, sOnc, isolated from culture medium (Liao, et al, 2003), as assayed by both the zymogram (FIG. 1b, left panel) and acid-insoluble method (data not shown). In contrast, rMOnc, which was produced without MetAP-*TG had no activity. These results reveal that the removal of N-terminal Met by engineered MetAP is crucial for the catalytic activity of onconase.

Similarly, the catalytic activity of rmRCL1-N2D was similar to that of the ribonuclease isolated from bullfrog liver (RCL1) or the ribonuclease purified from culture medium (sRCL1). However, the activity of rmRCL1 was not as high as rmRCL1-N2D, RCL1 or sRCL (FIG. 1b, right panel). Since RCL1 starts with MQN and RCL1-N2D starts with MQD, reduced activity of rmRCL1 was probably due to the partial deletion of terminal Gln, which occurs when the antepenultimate residue is a small or moderate amino acid (see Example 5). Therefore, for substrate proteins that start with MQ and followed by a small or moderate amino acid, it is desirable to change the antipenultimate residue to a bulky or charged amino acid (see Example 5), particularly Asp.

Example 8

In Vitro Catalytic Activities of MetAP Mutants

To test the catalytic activities of the engineered MetAPs in vitro, the mutants were purified and incubated with various peptide substrates. For oligopeptides ranging from tetra-to dodecapeptides with Ala at the penultimate site, the wild type MetAP and MetAP-*TG displayed high catalytic activity, while MetAP-*GG, MetAP-*TT and MetAP-GTG did not (Table 4).

For oligopeptides with Gln at the penultimate residue, the wild type and most engineered MetAPs did not exhibit significant catalytic activities. Among the MetAPs tested, MetAP-GTG exerted the most activity. The specific activity of MetAP-GTG on the dodecapeptide MQDWLTFQKKHI is 43% of that for MADWLTFQKKHI, which is identical to the N-terminal α-helix of rM-One. The low in vitro catalytic activity of the purified MetAP for MQD-initiated oligopeptide suggests that some factor(s), present in vivo, may be required for the removal of Met from bulky penultimate residues.

TABLE 4

In vitro catalytic activity of engineered MetAPs toward synthetic oligopeptides

| Substrate | Specific activity (unit/mg)[a] | | | | |
|---|---|---|---|---|---|
| | MetAP-YMQ(wt) | MetAP-*GG | MetAP-*TT | MetAP-*TG | MetAP-GTG |
| MADY (SEQ ID NO:7) | 138 ± 8 | 0.51 ± 0.01 | 0.38 ± 0.03 | 72 ± 10 | 1.68 ± 0.51 |
| MADYLT (SEQ ID NO:8) | 138 ± 6 | 0.29 ± 0.01 | 0.12 ± 0.01 | 116 ± 4 | 2.50 ± 0.42 |
| MQDYLT (SEQ ID NO:9) | 0.43 ± 0.01 | 0.29 ± 0.02 | 0.13 ± 0.01 | 0.42 ± 0.02 | 0.23 ± 0.01 |
| MADWLTFQKKHI (SEQ ID NO:5) | 85 ± 13 | 3.28 ± 0.04 | 1.00 ± 0.08 | 73 ± 15 | 9.80 ± 0.26 |
| MQDWLTFQKKHI (SEQ ID NO:6) | 0.62 ± 0.08 | 0.50 ± 0.02 | 0.25 ± 0.01 | 0.59 ± 0.07 | 4.24 ± 0.14 |

[a]One unit of activity is defined as one μmol of amino acid produced per min under the assay condition described in the text using pure Met as a standard.

A number of embodiments of the invention have been described. Nevertheless, it will be understood that various modifications may be made without departing from the spirit and scope of the invention.

What is claimed is:

1. An isolated cell comprising a methionine aminopeptidase that comprises an engineered version of SEQ ID NO:1, wherein residue 206 or 233 of SEQ ID NO:1 is substituted with an amino acid selected from the group consisting of Gly, Thr, Asp, Val and Asn, and wherein the methionine aminopeptidase is at least 90% identical to SEQ ID NO:1 outside of residues 168, 206 and 233.

2. The cell of claim 1 wherein the methionine aminopeptidase is at least 95% identical to SEQ ID NO:1 outside of residues 168, 206 and 233.

3. The cell of claim 1 that is a bacterial cell.

4. The cell of claim 1 that is an *E. coli*.

5. The cell of claim 1 that is an *E. coli* BL21(DE3) cell.

6. The cell of claim 1 that is a eukaryotic cell.

7. An isolated nucleic acid molecule comprising a sequence that encodes a methionine aminopeptidase that comprises an engineered version of SEQ ID NO:1, wherein residue 206 or 233 of SEQ ID NO:1 is substituted with an amino acid selected from the group consisting of Gly, Thr, Asp, Val and Asn, and wherein the methionine aminopeptidase is at least 90% identical to SEQ ID NO:1 outside of residues 168, 206 and 233.

8. The nucleic acid molecule of claim 7 wherein the methionine aminopeptidase is at least 95% identical to SEQ ID NO:1 outside of residues 168, 206 and 233.

9. The nucleic acid molecule of claim 7 wherein residue 233 of the polypeptide is substituted with Gly or Thr.

10. The DNA nucleic acid molecule of claim 7 wherein residue 206 of the polypeptide is substituted with Gly, Thr or Val.

11. The DNA nucleic acid molecule of claim 7 wherein both residues 206 and 233 of the polypeptide are substituted.

12. The DNA nucleic acid molecule of claim 7 wherein the polypeptide comprises the following substitutions at residues 206 and 233:
   (a) residue 206 is substituted with Gly and residue 233 is substituted with Gly;
   (b) residue 206 is substituted with Thr and residue 233 is substituted with Gly;
   (c) residue 206 is substituted with Thr and residue 233 is substituted with Thr; or
   (d) residue 206 is substituted with Val and residue 233 is substituted with Thr.

13. The nucleic acid molecule of claim 7 wherein the polypeptide further comprises a substitution at residue 168 of SEQ ID NO:1.

14. The DNA nucleic acid molecule of claim 13 wherein residue 168 of the polypeptide is substituted with an amino acid selected from the group consisting of Gly, Ser, Thr, Val, Asp and Glu.

15. The DNA nucleic acid molecule of claim 13 wherein residue 168 of the polypeptide is substituted with Gly or Thr.

16. The nucleic acid molecule of claim 7 that is an expression vector.

17. An isolated cell comprising the nucleic acid molecule of claim 7.

18. The cell of claim 17 that is a bacterial cell.

19. The cell of claim 17 that is an *E. coli*.

20. The cell of claim 17 that is an *E. coli* BL21(DE3) cell.

21. The cell of claim 17 that is a eukaryotic cell.

22. A method of removing the N-terminal methionine from a target protein comprising
   (i) introducing the nucleic acid molecule of claim 7 into a cell, wherein the cell comprises a nucleic acid molecule that encodes the target protein, and
   (ii) permitting the expression of the nucleic acid molecule of claim 14, whereby the target protein is cleaved.

23. A method of removing the N-terminal methionine from a target protein, comprising
   (i) introducing into a cell the nucleic acid molecule of claim 7 and also introducing into the cell a nucleic acid molecule that encodes the target protein, and
   (ii) permitting the expression of the nucleic acid molecule of claim 14 and the nucleic acid molecule that encodes the target protein,
   whereby the target protein is cleaved.

24. The method of removing the N-terminal methionine from a target protein of claim 23, wherein the nucleic acid molecule of claim 7 further comprises a second nucleic acid sequence that encodes the target protein.

25. The method of claim 22 wherein the amino acid residue next to the N-terminal methionine in the target protein is selected from the group consisting of Gln, Asn, Leu, Ile, Met and His.

26. The method of claim 22 wherein the amino acid residue next to the N-terminal methionine in the target protein is selected from the group consisting of Phe, Tyr and Trp.

27. The method of claim 22 wherein the amino acid residue next to the N-terminal methionine in the target protein is selected from the group consisting of Asp and Glu.

* * * * *

UNITED STATES PATENT AND TRADEMARK OFFICE
CERTIFICATE OF CORRECTION

| | | |
|---|---|---|
| PATENT NO. | : 7,109,015 B2 | Page 1 of 1 |
| APPLICATION NO. | : 10/813549 | |
| DATED | : September 19, 2006 | |
| INVENTOR(S) | : You-Di Liao | |

It is certified that error appears in the above-identified patent and that said Letters Patent is hereby corrected as shown below:

Column 29, lines 1, 4, 6, 20 and 24, the term "DNA" should be deleted.

Column 30, line 7, the claim reference numeral "14" should read --7--.

Column 30, line 14, the claim reference numeral "14" should read --7--.

Signed and Sealed this

Twelfth Day of December, 2006

JON W. DUDAS
*Director of the United States Patent and Trademark Office*